United States Patent [19]

Empie

[11] Patent Number: 4,636,470
[45] Date of Patent: Jan. 13, 1987

[54] RESOLUTION OF RACEMATES OF AMINO ACIDS

[75] Inventor: Mark W. Empie, Pleasantville, N.Y.

[73] Assignee: Stauffer Chemical Company, Dobbs Ferry, N.Y.

[21] Appl. No.: 641,887

[22] Filed: Aug. 17, 1984

[51] Int. Cl.$^4$ ............................................. C07P 41/00
[52] U.S. Cl. .................................... 435/280; 562/401
[58] Field of Search ................. 435/280, 803; 562/401

[56] References Cited

U.S. PATENT DOCUMENTS

| | | | |
|---|---|---|---|
| 3,813,317 | 5/1974 | Benoiton et al. | 435/280 |
| 3,878,043 | 4/1975 | Matta et al. | 435/280 |
| 3,907,638 | 9/1975 | Uzuki et al. | 435/280 |
| 3,926,726 | 12/1975 | Antonini et al. | 435/136 |
| 4,262,092 | 4/1981 | Bauer | 435/280 |
| 4,389,489 | 6/1983 | Preiss et al. | 435/280 |
| 4,439,524 | 3/1984 | Schutt | 435/280 |

OTHER PUBLICATIONS

Khmel'Nitski et al. (1984) Tetrahedron Vol. 40, No. 21, pp. 4425–4432.
Scheper et al. (1984) The Chemical Engineering Journal vol. 29, No. 2, pp. B31–B37.
Schutt et al. (1985) Biotechnology and Bioengineering vol. XXVII pp. 420–433.
Toi Bull. Chem. Soc. Japan 36(6) 739 (1963).
Castillo et al. Biochimica Biophysica Acta 253(2) 1971 pp. 358–369.
Chemical Abstracts No. 17, vol. 97 item #143123f, 1982 p. 537.
Martinex et al. Biochimica et Biophysica Acta 1981 vol. 658 pp. 76–101.
Chemical Abstracts No. 13, vol. 99 (1983) p. 467 item #103695d.

*Primary Examiner*—Sam Rosen
*Assistant Examiner*—William J. Herald
*Attorney, Agent, or Firm*—Paul J. Juettner

[57] ABSTRACT

Racemates of optically active amino acid substituted at the carbonyl position wherein the alpha amino acid nitrogen is underivatized and can be resolved using a two phase solvent system. The racemate is dissolved in a substantially water immiscible organic material which is a solvent for said amino acid racemate but not for the corresponding amino acids. The racemate is also dissolved in water (aqueous phase) and is in equilibrium with the racemate in the organic phase. One of the optical isomers of the amino acid racemate in the aqueous phase is enzymatically hydrolyzed to the corresponding amino acid and is recovered. The preferred product is L-phenylalanine.

20 Claims, No Drawings

RESOLUTION OF RACEMATES OF AMINO ACIDS

FIELD OF THE INVENTION

The present invention relates to a method for resolving racemic mixtures of amino acids wherein the carbonyl group is substituted and the alpha amino nitrogen is underivatized.

BACKGROUND OF THE INVENTION

It is well known that racemic mixtures of N-acyl D,L-amino acids can be resolved by the use of mold acylase enzyme (U.S. Pat. No. 3,907,638). In this process, water, N-acyl D,L-amino acid and acylase are stirred in organic solvent at a pH and temperature suitable for acylase activity. After reaction, the acylase is in the aqueous phase, the optically active N-acyl amino acid and the acid formed by deacylation are in the organic phase and the desired deacylated amino acid is in the aqueous phase as solute or precipitated as a solid. These procedures are effective for N-acyl amino acids using the N-acyl group as the means for resolution. This patent does not teach resolution of racemic mixtures of carbonyl substituted amino acids which are not N-acyl substituted.

It is also known that esters of amino acids with large hydrophobic side chains attached to the alpha carbon atom such as L-phenylalanine can be hydrolyzed by various enzymes, such as chymotrypsin. The specificity of the enzyme for hydrolyzing the ester of the L-isomer forms the basis of a process for the enzymatic resolution of racemic mixtures of phenylalanine (U.S. Pat. No. 3,813,317 and the references cited therein as well as U.S. Pat. No. 3,878,043). In U.S. Pat. No. 3,813,317, an enzyme such as chymotrypsin is used to resolve an aqueous racemic mixture of ring substituted phenylalanines. The reaction is carried out in aqueous solution. A balance had to be struck between a low concentration of ester needed for good enzyme activity and a high concentration needed for easier product recovery.

In U.S. Pat. No. 3,878,043, an intermediate of L-DOPA is resolved into the L-isomer by hydrolysis of the ester group. The hydrolysis is conducted in an aqueous medium preferably including a water soluble organic solvent such as an alkanol. The D-isomer product is separated by contacting the aqueous solution with an organic solvent which takes up the D-isomer. The aqueous solution is then concentrated and the L-isomer separated.

This method of resolving amino acid esters suffers from several inherent problems. During the course of the hydrolysis, acid is liberated from the newly generated carboxyl group. As the enzyme activity is pH sensitive, the acid must be continuously neutralized to prevent the pH from dropping sufficiently low to seriously effect enzyme activity. The D-amino acid ester acts as an inhibitor to the enzyme used in the hydrolysis reaction. As the resolution proceeds, the concentration of the D-amino acid ester increases relative to the L-ester, further decreasing enzyme activity.

For an industrial process, it is desirable to process high concentrations of racemic mixtures of amino acid esters. However, it is known that high concentrations of such amino acid esters i.e. phenylalanine, can be catalyzed by the enzyme to form insoluble peptides. These peptides lower product purity and yields.

SUMMARY OF THE INVENTION

In accordance with the present invention, the problems inherent in the resolution of racemates of carbonyl substituted amino acids can be overcome by contacting a solvent solution of the carbonyl substituted amino acid racemate dissolved in a substantially water immiscible organic material with water; and, while portions of the so formed organic phase and aqueous phase are in contact, selectively hydrolyzing in at least a portion of the aqueous phase one of the isomers of the racemate with an enzyme capable of selectively hydrolyzing that optical isomer to the corresponding amino acid optical isomer. The desired amino acid can be recovered by known techniques such as by precipitation from the aqueous solution.

By using the two phase solvent system, the requirement for continuous neutralization and the problems of enzyme activity inhibition such as caused by the buildup of the unresolved isomer and peptide formation can be avoided.

DETAILED DESCRIPTION OF THE PRESENT INVENTION

The present invention is directed to resolving optically active isomers of amino acids with underivatized alpha amino nitrogen. The carbonyl group of these acids is substituted with a moiety hydrolyzable such as by an enzyme. These carbonyl substituted amino acids can be represented by the formula:

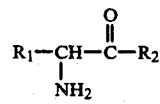

wherein $R_1$ can be straight or branched chain alkyl, alkylthio, alkoxy; benzyl and indoylalkyl and the hydroxy, halo, alkyl and nitro substituted derivatives thereof; $R_2$ is selected from the group consisting of $YR_3$, wherein Y is oxygen or sulfur, or $NHR_4$; $R_3$ can be straight or branched chain aliphatic radicals having from 1 to about 8 carbon atoms, aryl of up to 3 fused rings and the hydroxy, halo, alkyl and nitro substituted derivatives thereof and $R_4$ can be the same as defined in $R_3$ and hydrogen. As used herein the term alkyl used alone or in derivative form such as alkoxy, alkylthio, indoylalkyl and the like are intended to include groups ranging from 1 to about 8 carbon atoms. As used herein, the term "carbonyl substituted" is intended to mean that the carbonyl group attached to the alpha carbon atom is substituted as is shown in the formula in this paragraph.

Examples of the represented parent amino acids, i.e. as if $R_2$ were hydroxyl, include valine, leucine, isoleucine, methionine, phenylalanine, tyrosine, tryptophan, 3,4-dihydroxyphenylalanine, 2,4-dihydroxy-phenylalanine; 3,4-methylenedioxyphenylalanine, 3,4-dimethoxyphenylalanine; 3(4)-methoxy-4(3)-hydroxyphenylalanine; 3,4-isopropylidenedioxyphenylalanine; 3,4-cyclohexylidenedioxyphenylalanine, 5-hydroxytryptophan; 5-methyltryptophan and 3,4,5-trihydroxyphenylalanine.

The amino acids used are in the form of hydrolyzable derivatives. The moiety attached to the carbonyl group of the amino acid must be hydrolyzable by an enzyme to form the corresponding optical isomer of the free amino acid. The hydrolyzable group must not be of sufficient molecular weight or structure to cause the amino acid modified with the group to become insoluble in the water in which the hydrolysis must occur. Some of the groups which are included in the term "hydrolyzable" include the preferred ester, as well as primary and secondary amides ($R_2$ can be —$NH_2$, and —NHR), and thioesters (Y=S). The ester groups can be straight or branched chain aliphatic of from $C_1$ to $C_8$, aromatic up to three fused rings and substituted derivatives thereof such as halo, hydroxy, alkyl, nitro and the like. The amides are preferably prepared from straight or branched chain aliphatic amines of from $C_1$ to $C_8$, aryl or up to 3 fused rings and the alkyl, halo, hydroxy and nitro substituted derivatives thereof.

The main criteria for the hydrolyzable carbonyl-substituted amino acids is that the D,L-isomers are soluble in water and organic solvent, and one of the optical isomers is hydrolyzable at the carbonyl group to produce the corresponding amino acid. Preferably, the hydrolyzable group is the ester and more preferably the ester is methyl or ethyl.

Preferably, the amino acid is phenylalanine or ring substituted derivatives thereof. The ring substituents can include hydroxy, alkyl, halo and nitro groups. The preferred hydrolyzable group is the ester. As used in this specification halo is intended to include fluoro, chloro, bromo and iodo unless otherwise stated. Preferably the ester is the methyl or ethyl ester. The remaining description of the invention will be discussed in connection with the preferred amino acid, phenylalanine, and its esters though the teachings apply equally to the other named amino acids and hydrolyzable derivatives.

The racemate of carbonyl substituted phenylalanine is dissolved in a substantially water immiscible inert organic material which is a solvent for the racemate but is not a solvent for the corresponding amino acid. By immiscible it is intended to mean that the organic material is miscible in the water up to no more that 15% under the conditions of reaction. The organic material can be any water immiscible or partially miscible organic solvent which is non-reactive with the carbonyl substituted amino acid, the amino acid, the hydrolytic enzyme or have substantially no inhibitory effect on the enzyme activity. The organic solvents can be illustrated by toluene, methylene chloride, cyclohexanone, ethyl acetate, butyl acetate, butanol, and the like, with toluene being preferred. The carbonyl substituted amino acid also can act as the solvent itself. The solvent to water volume ratio can range from about 1:10 to about 10:1 with a ratio of from about 2:1 to about 1:2 being preferred. The carbonyl substituted amino acid, e.g. phenylalanine ester, content of the organic solvent can range from about 100% to about 5%, with from about 30% to about 10% on a weight per volume basis being preferred.

Carbonyl substituted amino acids such as the ester can be used in the form of an inorganic salt. The inorganic salts of carbonyl-substituted amino acid are water soluble not organic solvent soluble. The inorganic salts can be specifically prepared or be the result of other processing such as racemization. To use the racemate in the salt form, the racemate is extracted into an immiscible organic material by neutralizing the salt with a sufficient amount of base such as sodium hydroxide to extract the amino acid into the organic material. The carbonyl substituted amino acid thus becomes organic solvent soluble. The aqueous phase containing the inorganic salt can be removed or used as the aqueous phase for the enzyme hydrolysis. It is essential to the operation of the process of the invention that a substantial portion of the non-hydrolyzable isomer remaining after hydrolysis collect essentially in the organic phase during hydrolysis. By these means, the nonhydrolyzed isomer of the racemate, which acts as an inhibitor to the esterase (protease) enzyme can be kept isolated therefrom while the hydrolysis reaction is proceeding, and the amount of such isomer increases in the organic phase sufficient under the conditions of reaction to extract at least 50% of the carbonyl substituted amino acid salt into the organic phase due to the resolution. By "neutralized" is meant a pH within the range of from about 5.0 to about 8.0.

Following extraction, an enzyme which can selectively hydrolyze the carbonyl substituted amino acid to the corresponding amino acid, e.g. an esterase (protease), is added to the aqueous phase. The enzyme can be selected to resolve i.e. hydrolyze, either the D or the L forms as desired but must be specific to one in order for the resolution to be effected. Proteases will hydrolyze the ester, amide or thioester substituted amino acids listed hereinbefore. The proteases include chymotrypsin (in all forms), fungal protease, pancreatic extracts such as pancreatin, papain, subtilisin as well as commercially available enzymes such as Pronase TM brand and yeast protease. One of the preferred enzymes for converting the ester of L-phenylalanine into its corresponding amino acid is chymotrypsin. As is obvious to a skilled artisan, care should be taken to avoid excess loss of enzyme activity due to the use of reaction conditions which can adversely effect enzyme activity.

The enzyme can be added free or immobilized on a matrix or contained in an insolubilized enzyme column. In the case of a system utilizing the organic material and the aqueous phase in a single reactor, the enzyme can be added to the aqueous phase and the hydrolysis reaction allowed to proceed in that fashion. The enzyme could also be added in an immobilized state by stirring or suspending the immobilized enzyme in the aqueous portion of the reactor. The aqueous phase can also be pumped through an immobilized enzyme either contained totally within the aqueous phase or preferably external to the reactor. In one preferred form of the present invention, portions of the aqueous phase are pumped out of the reaction vessel, through a filter to remove any solids, into an enzyme column where the hydrolysis reaction occurs followed by pumping the effluent from the column back through the organic phase and the aqueous phase. Any amino acid formed by the hydrolysis reaction can then be separated from the aqueous phase by precipitation. This is preferably accomplished at the filter. Part of the aqueous phase remains in contact with the solvent phase to replenish the unresolved carbonyl substituted amino acid.

In another embodiment, immobilized enzyme is suspended in the aqueous phase and the hydrolysis reaction is then conducted while the aqueous phase is in contact with the organic phase under the appropriate conditions for enzymatic hydrolysis such as at temperatures ranging from about 30° C. to about 55° C. After the hydrolysis reaction has proceeded to the desired end point, the aqueous phase is separated from the organic phase, the immobilized enzyme is separated, such as by filtration or centrifugation, and the desired amino acid isolated from the aqueous phase by normal methods, such as by crystallization at temperatures appropriate for the amino acid to be separated, such as from about 0° C. to about 10° C. and preferably from about 2° C. to about 6° C., for phenylalanine. In order to prevent the immobilized enzyme from becoming inactivated by blocking the pores on the support with precipitated amino acid, this embodiment is preferably operated under conditions wherein the concentration of amino acid is at or below the limits of solubility at the reaction conditions used.

The immobilized enzyme can be carried on any one of a number of supports well known to the prior art such as polymers of each of acrylic acid, styrene, divinyl benzene, polyethylene terephthalate, agarose and dextran. The immobilization support to be used can be easily determined by a skilled artisan as long as the support is not antagonistic to the system. The immobilized enzyme can be used for numerous runs so that the economics of the process can be improved by such use. The enzyme and substrate ratio can be within the range of from about 1:10 to about 1:10000 with a ratio of from about 1:2000 being preferred. The enzyme amount can be easily determined by a skilled artisan relative to accomplishing a desired rate of hydrolysis. Preferably, the enzyme is used in an amount sufficient to hydrolyze about 50% of the total of one of the optical isomers of the racemate in the two phase system to the corresponding amino acid within 3 hours.

The temperature and pH conditions within the aqueous phase or within the immobilized enzyme column are maintained under such conditions as to be favorable to the hydrolysis reaction with the enzyme being used. In connection with enzymes in general and chymotrypsin in particular, the temperature of reaction can range from about 0° C. to about 60° C. with from about 18° C. to about 50° C. being preferred. The pH of the reaction system can range from about 5 to about 8 with a preferred pH ranging from about 6.0 to about 7.5. Other conditions would be obvious to a skilled artisan depending on the enzyme utilized.

One of the important features of the present invention is the ability for the system to maintain pH during hydrolysis even though an acid is being formed. As the reaction proceeds, the protease hydrolyzes the carbonyl substituted amino acid, e.g. the L-phenylalanine ester, in the aqueous phase to the L-amino acid, e.g. L-phenylalanine. An equilibrium between the organic phase, which contains a majority of the racemate and the aqueous phase, which contains a small part of the racemate, is thus upset by the reduction of the isomer being hydrolyzed, e.g. the L-phenylalanine ester. To reestablish the equilibrium, the isomer ester being hydrolyzed, e.g. L-phenylalanine ester, is partitioned from the organic phase into the aqueous phase. In this manner, the isomer ester which is to be hydrolyzed, e.g. the L-phenylalanine ester is continuously drawn from the organic phase into the aqueous phase until substantially all of that isomer is hydrolyzed. The unhydrolyzed isomer ester, e.g. the D-isomer ester, remains in the organic layer and the concentration of the unhydrolyzed isomer in the aqueous layer is kept low so that concentrations of the inhibiting isomer in the aqueous phase do not build up. By this means, automatic partition of the D,L-carbonyl substituted amino acid isomers is obtained while avoiding enzyme activity inhibition. In the course of partitioning the L-isomer, e.g. the L-phenylalanine ester, from the D,L-isomer, e.g. the D,L-phenylalanine ester, from the organic phase to the aqueous phase, the L-isomer, e.g. the L-phenylalanine ester, of the free amino group is protonated. This provides a buffering action needed to neutralize the acid produced from the ester hydrolysis. Thus, for each molecule of L-isomer hydrolyzed, one hydrogen ion is produced and one molecule of free amine is extracted into the aqueous phase. The free amine absorbs a hydrogen ion, keeping the pH of the aqueous phase essentially constant without having to add an external neutralizing agent though an external weak neutralizing agent could be added if desired.

The pH of the aqueous phase controls the amount of carbonyl substituted amino acid in the aqueous phase. The lower the pH, the more is contained in the aqueous portion. This allows for control of the enzymatic reaction rate. Because of the lower concentration of the L-amino acid in the aqueous phase, the formation of phenylalanine peptide is controlled.

The control of the equilibrium rate on partition from the organic phase into the aqueous phase as well as the pH control is also maintained in like manner when the hydrolysis is conducted external to the vessel containing the aqueous phase and the organic phase.

After substantially all of the L-isomer is separated from the organic phase, the concentrated D-isomer can be racemized by any known method such as high temperature or the use of strong base. The hydrolysis can then be continued in the normal fashion.

The process can be conducted statically or under agitation. Agitation can be strong enough to form finely dispersed droplets of one phase in the other. The two phase system should not be agitated sufficiently to form a stable emulsion as the two phases must be separated to isolate the product. The concentration of the desired amino acid must be below the limits of solubility under the conditions of reaction. If the amino acid does precipitate, it may be removed by conventional methods. Agitation formed by pumping fractions in and out of the reactor is acceptable.

The process of the invention can be operated as a batch process or continuously, as desired. In a continuous process, precipitated L-amino acid can be continuously removed such as by filtration of the aqueous phase. Portions of the organic phase can be removed, racemized and returned to provide more L-isomer or an organic solution can be prepared by dissolving the racemate in water, contacting with organic solvent, neutralizing and separating off the aqueous phase. If a racemizing agent is used that can retard the effectiveness of the enzyme, good manufacturing practices may dictate removal of the agent before resolution.

Amino acids of the type formed by the present invention are well known and have many well known uses. L-phenylalanine is a well known material which finds uses in such areas as parenteral nutrition, amino acid supplements and drug intermediates. Particularly, L-phenylalanine has found use as a precursor in preparing aspartame. The products of the present invention are of sufficient purity to allow for such uses.

The non-resolved isomer of the carbonyl substituted amino acid can also be recovered from the organic solvent by any known separation technique, such as distillation, precipitation, or extraction as a hydrochloride salt. These HCl salts can be isolated and sold as such or the hydrolyzable group hydrolyzed. After hydrolysis has proceeded to the desired point, the aqueous solution can be concentrated and neutralized whereby the D-isomer amino acid precipitates.

The present invention will be further illustrated in the Examples which follow.

EXAMPLE 1

A mixture of 1.15 grams of D,L-phenylalanine methyl ester in 2.5 milliliters of water was added to 5.0 milliliters of ethyl acetate. The pH was adjusted to 6.5 with 2.5 milliliters of sodium hydroxide. Two milligrams of chymotrypsin was added and the reaction was stirred gently at room temperature. A white precipitate appeared after 1.5 hours. The precipitate was isolated after 2 hours yielding 0.22 grams with an optical rotation equivalent to 98% pure L-phenylalanine.

EXAMPLE 2

A 0.2 molar solution phenylalanine methyl ester in 10 milliliters of water was prepared. Toluene was added and the pH of the system adjusted to 7.0 with sodium hydroxide. Chymotrypsin in the amount of 1 milligram was added. The concentration of phenylalanine in the aqueous phase was monitored. The initial concentration was 0.05 molar and the final concentration at the end of the hydrolysis was 0.15 molar, consistent with only one isomer being extracted.

EXAMPLE 3

A solution of 2.29 grams of D,L-phenylalanine methyl ester hydrochloride in 10 milliliters of water was prepared. Ten milliliters of toluene was added and the pH of the aqueous phase of the biphase mixture was adjusted to 6.8 with sodium hydroxide. The mixture was allowed to separate and the aqueous phase (or lower phase) was connected to a pump via tubing. The pump was then connected to a filter. A portion of the aqueous phase was pumped through the filter into a column containing chymotrypsin enzyme immobilized on Sepharose TM 4B (Pharmacia). The effluent from the column was then pumped back into the biphase reaction mixture. The initial pH of the enzyme column effluent was 6.2. After 5 hours the pH increased to 6.8. The pH in the biphase reaction mixture was constant at 6.8. L-phenylalanine precipitated in the aqueous phase and was recovered by the filter with an overall yield of 85% based on the theoretical amount of recoverable phenylalanine after correcting for water saturation.

EXAMPLE 4

To 50 milliliters of a 3% weight per volume presaturated solution of L-phenylalanine was added 10.0 grams D,L-phenylalanine ethyl ester hydrochloride and 50 milliliters of toluene. The biphase mixture was neutralized to a pH of 6.8 with 50% sodium hydroxide and 25 milligrams chymotrypsin enzyme was added. The reaction proceeded for 3.5 hours whereupon the precipitate which formed during the reaction was filtered out and washed with small amounts of water. A total of 1.9 grams of L-phenylalanine was obtained with 98% purity by optical rotation.

The toluene from the reaction was separated from the aqueous layer and the D-phenylalanine ester contained therein was racemized. The toluene and racemized ester were returned to the aqueous phase where a second hydrolysis reaction was undertaken to further resolve the racemized D,L,-phenylalanine ester. A second precipitate was obtained in an amount of 1.5 grams which was 96% L-phenylalanine.

EXAMPLE 5

D,L-phenylalanine methyl ester hydrochloride was extracted into toluene by neutralization with sodium hydroxide to give a 9.2% solids solution. An aliquot of 300 milliliters was placed in contact with 210 milliliters of water. The pH of the mixture was adjusted to 6.8. The temperature was raised to 40° C., chymotrypsin immobilized as in Example 3 was added and the reaction mixture was stirred for 6 hours until the reaction was complete. The enzyme was filtered out and the aqueous portion separated. The aqueous portion was cooled overnight at 4° C. 4.6 grams of precipitated L-phenylalanine of 92% purity by optical rotation was obtained. This represents 84% yield after correcting for water saturation.

In view of the foregoing, it can be seen that the advantages of the invention are obtained.

As various changes could be made in the above processes without departing from the scope of the invention, it is intended that all matter contained in the above description shall be interpreted as illustrative and not in a limiting sense.

What is claimed is:

1. A process for resolving a racemate of optically active amino acids substituted at the carbonyl position and wherein the alpha amino acid nitrogen is underivatized comprising:
   (a) preparing a two phase system of a racemate of an amino acid substituted at the carbonyl position wherein the alpha amino acid nitrogen is underivatized by dissolving in a substantially water immiscible organic material which is a solvent for said amino acid racemate, but not for the corresponding unsubstituted amino acids, adding water to form an aqueous phase wherein the racemate dissolved in the aqueous phase is in equilibrium with the racemate in the organic phase a majority of the racemate being dissolved in the substantially water immiscible organic solvent phase;
   (b) selectively hydrolyzing with an enzyme one of the optical isomers of the amino acid racemate in the aqueous phase to the corresponding amino acid; and
   (c) recovering the amino acid.

2. The process according to claim 1 wherein said enzyme is in said aqueous solution.

3. The process according to claim 2 wherein said aqueous solution and said organic material are maintained in contact for a period of time and under conditions facilitating the enzyme hydrolysis.

4. The process as recited in claim 1 wherein the aqueous phase is in contact with the organic phase to replenish the isomer in the aqueous phase which was removed by hydrolysis.

5. The process as recited in claim 1 wherein the amino acid substituted at the carbonyl position is an amino acid ester.

6. The process according to claim 5 wherein the amino acid ester is an ester of phenylalanine.

7. The process according to claim 5 wherein the ester is a $C_1$–$C_8$ ester.

8. The process according to claim 1 wherein the ester is methyl or ethyl.

9. The process according to claim 1 wherein the enzyme is chymotrypsin.

10. The process according to claim 1 wherein the optical isomer being hydrolyzed is the L-isomer.

11. The process according to claim 1 wherein the organic material is selected from the group consisting of toluene, methylene chloride, cyclohexanone, butyl acetate, ethyl acetate, and mixtures thereof.

12. The process according to claim 1 wherein the organic material is toluene.

13. The process according to claim 1 wherein the enzyme is immobilized.

14. The process according to claim 1 wherein the hydrolysis is accomplished by passing the aqueous solution through an enzyme which is external to the contacted aqueous solution and organic material.

15. The process according to claim 14 wherein the enzyme is immobilized.

16. The process according to claim 1 wherein the recovered amino acid is L-phenylalanine.

17. The process according to claim 1 wherein the organic material to water volume ratio ranges from about 10:1 to about 1:10.

18. The process according to claim 1 wherein the organic material to water volume ratio ranges from about 2:1 1:2.

19. The process according to claim 1 wherein the racemate content of the organic material can range from about 100% to about 5%.

20. The process according to claim 19 wherein the racemate content of the organic material can range from about 30% to about 10%.

* * * * *